(12) United States Patent
Dodd et al.

(10) Patent No.: US 7,174,207 B2
(45) Date of Patent: Feb. 6, 2007

(54) IMPLANTABLE DEFIBRILLATOR HAVING REDUCED BATTERY VOLUME

(75) Inventors: Joanna Dodd, Pasadena, CA (US); Hisashi Tsukamoto, Santa Clarita, CA (US); Mikito Nagata, Saugus, CA (US)

(73) Assignee: Quallion LLC, Sylmar, CA (US)

( * ) Notice: Subject to any disclaimer, the term of this patent is extended or adjusted under 35 U.S.C. 154(b) by 174 days.

(21) Appl. No.: 10/949,063

(22) Filed: Sep. 23, 2004

(65) Prior Publication Data

US 2006/0064130 A1    Mar. 23, 2006

(51) Int. Cl.
*A61N 1/39* (2006.01)

(52) U.S. Cl. .......................................................... 607/5

(58) Field of Classification Search ................... 607/2, 607/5
See application file for complete search history.

(56) References Cited

U.S. PATENT DOCUMENTS

| | | | |
|---|---|---|---|
| 5,028,500 A | 7/1991 | Fong et al. | |
| 5,153,082 A | 10/1992 | Ogino et al. | |
| 5,244,757 A | 9/1993 | Takami et al. | |
| 5,312,611 A | 5/1994 | Takami et al. | |
| 5,405,363 A | 4/1995 | Kroll et al. | |
| 5,407,444 A | 4/1995 | Kroll | |
| 5,411,537 A | 5/1995 | Munshi et al. | |
| RE34,991 E | 7/1995 | Yoshino et al. | |
| 5,547,654 A | 8/1996 | Machida et al. | |
| 5,591,212 A * | 1/1997 | Keimel | 607/5 |
| 5,612,155 A | 3/1997 | Takami et al. | |
| 5,631,100 A | 5/1997 | Yoshino et al. | |
| 5,697,953 A | 12/1997 | Kroll et al. | |
| 5,744,264 A | 4/1998 | Barker | |
| 5,836,973 A * | 11/1998 | Kroll | 607/5 |
| 5,888,670 A | 3/1999 | Kawakami | |
| 5,900,336 A | 5/1999 | Kabata et al. | |
| 6,019,802 A | 2/2000 | Ishizuka et al. | |
| 6,022,518 A | 2/2000 | Yamazaki et al. | |
| 6,037,095 A | 3/2000 | Miyasaka | |

(Continued)

FOREIGN PATENT DOCUMENTS

EP    0 474 183 B1    12/2000

(Continued)

OTHER PUBLICATIONS

Tsukamoto et al., Implantable Rechargeable Lithium Ion Batteries for Medical Applications, Fall 2003, http://www.quallion.com/pdf/2004 IBA Hisashi.pdf☐☐.*

(Continued)

*Primary Examiner*—Robert Pezzuto
*Assistant Examiner*—Yun Haeng Lee
(74) *Attorney, Agent, or Firm*—Gavrilovich Dodd & Lindsey (57) ABSTRACT

A defibrillator is disclosed. The defibrillator includes a secondary battery having a volume less than 5 cc. One or more capacitors are configured to store electrical energy from the battery in an amount sufficient to provide a patient with one or more defibrillation shocks. A processing unit is configured to control the storage of electrical energy in the one or more capacitors and to control the discharge of the electrical energy from the one or more capacitors. The battery can have a total volume of less than 4 cc or less than 3 cc.

26 Claims, 4 Drawing Sheets

U.S. PATENT DOCUMENTS

| | | | |
|---|---|---|---|
| 6,040,087 A | 3/2000 | Kawakami | |
| 6,087,044 A | 7/2000 | Iwase et al. | |
| 6,245,464 B1 | 6/2001 | Spillman et al. | |
| 6,261,722 B1 | 7/2001 | Dasgupta et al. | |
| 6,287,729 B1 | 9/2001 | Tamaki et al. | |
| 6,294,291 B1 | 9/2001 | Ozaki et al. | |
| 6,300,012 B1 | 10/2001 | Iijima et al. | |
| 6,309,777 B1 | 10/2001 | Ohta et al. | |
| 6,337,156 B1 | 1/2002 | Narang et al. | |
| 6,342,319 B1 | 1/2002 | Kuboki et al. | |
| 6,350,544 B1 | 2/2002 | Takami et al. | |
| 6,350,546 B1 | 2/2002 | Gan et al. | |
| 6,355,377 B1 | 3/2002 | Sheem et al. | |
| 6,383,686 B1 | 5/2002 | Umeno et al. | |
| 6,395,427 B1 | 5/2002 | Sheem et al. | |
| 6,403,259 B1 | 6/2002 | Kitagawa et al. | |
| 6,420,070 B1 | 7/2002 | Kasamatsu et al. | |
| 6,455,199 B1 | 9/2002 | Kitagawa et al. | |
| 6,479,426 B2 | 11/2002 | Ryu et al. | |
| 6,549,807 B1 | 4/2003 | Kroll | |
| 6,552,511 B1 * | 4/2003 | Fayram | 320/103 |
| 6,617,075 B2 | 9/2003 | Mao et al. | |
| 6,852,449 B2 | 2/2005 | Nagata et al. | |
| 6,937,894 B1 * | 8/2005 | Isaac et al. | 607/5 |
| 2002/0029464 A1 | 3/2002 | Iijima et al. | |
| 2002/0034685 A1 | 3/2002 | Sato et al. | |
| 2002/0037455 A1 | 3/2002 | Tani et al. | |
| 2002/0039684 A1 | 4/2002 | Matsubara et al. | |
| 2002/0061440 A1 | 5/2002 | Suzuki et al. | |
| 2002/0064712 A1 | 5/2002 | Sekino et al. | |
| 2003/0068555 A1 | 4/2003 | Naruoka | |
| 2003/0113632 A1 | 6/2003 | Brown et al. | |
| 2003/0152835 A1 | 8/2003 | Desgupta et al. | |

FOREIGN PATENT DOCUMENTS

| | | |
|---|---|---|
| EP | 1 089 366 A1 | 4/2001 |
| EP | 0 803 926 B1 | 12/2001 |
| EP | 0 903 799 B1 | 3/2003 |
| JP | 04-115457 | 4/1992 |
| JP | 04-237971 | 8/1992 |
| JP | 04-342966 | 11/1992 |
| JP | 05-074462 A2 | 3/1993 |
| JP | 05-283060 A2 | 10/1993 |
| JP | 06-044959 A2 | 2/1994 |
| JP | 06-111818 | 4/1994 |
| JP | 06-163032 | 6/1994 |
| JP | 08-031419 A2 | 2/1996 |
| JP | 08-083608 | 3/1996 |
| JP | 08-306390 A2 | 11/1996 |
| JP | 2762881 B | 3/1998 |
| JP | 10-188959 A2 | 7/1998 |
| JP | 10-302794 A2 | 11/1998 |
| JP | 11-054123 A2 | 2/1999 |
| JP | 2000-228193 A2 | 8/2000 |
| JP | 2000-251890 A2 | 9/2000 |
| JP | 2000-260424 A2 | 9/2000 |
| JP | 2000-294230 A2 | 10/2000 |
| JP | 2000-323174 A2 | 11/2000 |
| JP | 2002008655 A2 | 1/2002 |
| WO | WO 90/13924 | 11/1990 |
| WO | WO 98/40923 A1 | 9/1998 |
| WO | WO 02/41417 A1 | 5/2002 |

OTHER PUBLICATIONS

Dodd, J. et al., Implantable Rechargeable Lithium Ion Batteries for Medical Application: Neurostimulation and Cardiovascular Devices, The Electrochemical Society, Inc., Abs. 422, 204th Meeting (2003).

Holmes, Appendix: Sizing the Battery, The Battery, pp. 219-220.

Sears, S.F., Understanding Implantable Cardioverter Defibrillator Shocks and Storms: Medical and Psychosocial Considerations for Research and Clinical Care, Clin. Cardio., (2003), 26, 107-111.

Mesocarbon Microbeads Renoves® M Series, MCMB, http://www.ashland-suedchemie.de/en/english/c_produkte/cprodukteMesocarbon Microbeads Renoves® M Series, MCMB, http://www.ashland-suedchemie.de/en/english/c_produkte/cprodukte5.htm.

Du, C. Influence of Particle Structure on Electrochemical Character of Composite Graphite, Journal of University of Science and Technology Beijing, (2003), 61-64, 10, 1, China.

The Graphite, Types of Graphite, http://www.graphite.com/grafote_i.htm , 3 pages, 2004.

Hitachi Chemical Website—Anode Material for Lithium Batteries Section.

* cited by examiner

IMPLANTABLE DEFIBRILLATOR HAVING REDUCED BATTERY VOLUME

REFERENCE TO RELATED APPLICATIONS

This application is related to U.S. patent application Ser. No. 10/264,870; filed on Oct. 3, 2002; entitled "Anode for a Nonaqueous Battery" which claims priority to U.S. Provisional Patent application Ser. No. 60/406,846; filed on Aug. 29, 2002. Each of the above applications is incorporated herein in its entirety.

FIELD

The present invention relates to medical device and more particularly to an implantable defibrillator.

BACKGROUND

Implantable cardioverter defibrillators (ICD) are used to provide defibrillation shocks that correct ventricular fibrillation and other arrhythmias that do not respond to lower-energy therapies. The defibrillation shocks are generated by using a low voltage battery to charge a capacitor. The batteries are generally primary batteries. One drawback of primary batteries is the need to explant the device in order to replace the battery after it has discharged its energy. Secondary batteries that can be recharged through the skin may reduce the need to explant a defibrillator in order to change the battery.

Secondary batteries have not been adopted by defibrillator manufacturers due to their high levels of self-discharge and high levels of calendar fade. Self-discharge is a measure of the rate at which a battery discharges when stored unused. It is a temporary loss, and the capacity discharged can be regained by charging the battery again. Batteries with high levels of self-discharge must be recharged frequently even when the battery is not used. As a result, a patient having a defibrillator with one of these batteries would need to frequently recharge the battery and would risk having a defibrillation event when the battery does not have the required capacity.

Calendar fade measures the amount of rechargeability that is permanently lost over the life of the battery. For instance, a battery with a high levels of calendar fade shows a drop in the maximum capacity to which the battery can be charged with the passage of time. As a result, the frequency with which the battery must be recharged increases over the life of the battery. Further, high levels of calendar fade can result in the need to explant the ICD and replace the battery. For the above reasons, there is a need for a defibrillator having an extended life and reduced maintenance requirements.

SUMMARY

A defibrillator is disclosed. The defibrillator includes a secondary battery having a volume less than 5 cc. One or more capacitors are configured to store electrical energy from the battery in an amount sufficient to provide a patient with one or more defibrillation shocks. A processing unit is configured to control the storage of electrical energy in the one or more capacitors and to control the discharge of the electrical energy from the one or more capacitors. In some instances, the battery has a total volume of less than 4 cc, less than 3 cc or in a range of 3 cc to 4 cc.

The battery can have self-discharge characteristics for which the temporary capacity loss due to self-discharge is less than 6% of the cell discharge capacity, after being stored fully charged at 37° C. for six months where each month has 30 days. Additionally or alternately, the battery can have calendar fade characteristics that provide a permanent discharge capacity loss of less than 11% after being stored fully charged at 37° C. for twelve months. Additionally or alternately, the battery can have at least 87% discharge capacity retention after being repeatedly charged and discharged for more than 1000 cycles where each cycle includes charging to 4.1 V with constant current at a 0.5 C rate followed by constant voltage charging at 4.1 V to a 0.05 C cutoff current followed by discharge to 2.5 V at a 0.5 C rate.

In one embodiment of the defibrillator, the battery includes one or more anodes that include an anode active material represented by $C_6Li_n$ with n=0 before the initial charge and one or more cathodes that include a cathode active material represented by $Li_{1-p}MO_2$ where M is one or more metals and with p=0 before the initial charge. The anode active material and the cathode active material being present in an amount such that at full charge n increases to 0.5 to 0.8 and p increases to 0.6 to 0.8.

DESCRIPTION

A defibrillator having a secondary battery is disclosed. The battery has a surprisingly low self-discharge. For instance, embodiments of the battery can be stored unused and fully charged at 37° C. (simulating body temperature) for six months with less than 6% of discharge capacity temporarily lost due to self-discharge. Further, the battery has a surprisingly long calendar life. For instance, embodiments of the battery stored fully charged at 37° C. for 6 yrs show a predicted ability to be recharged to at least 80% of the original capacity and in some instances, at least 85% of the original capacity. As a result, the defibrillator retains the benefits of rechargeability while overcoming the challenges of high self-discharge and high calendar-fade.

The batteries can also show a high cycle life. For instance, embodiments of the battery repeatedly cycled between 2.7 V and 4.1 V at a C/2 rate at 37° C. show at least 87% capacity retention after 1000 cycles. The high cycle life reduces the effects of repeated battery recharges. The ability to repeatedly recharge the battery allows the battery to have a reduced size. The primary batteries of prior defibrillators had to be large in order to provide the defibrillator with the desired life. However, the long cycle life and low calendar fade associated with the disclosed battery allow the battery size to be reduced. For instance, the battery can be less than or equal to 5 cc, 4 cc or 3 cc. In some instances, the battery has a total volume of between about 3 cc and about 4 cc. Because batteries take up a large portion of the space in a defibrillator, these battery size reductions allow for significant reductions in the size of a defibrillator.

Defibrillators generally provide monitoring and pacing functions in addition to the defibrillation shocks. The reduced size of the battery does not interfere with the ability of the batteries to provide the energy needed for the defibrillation shocks and monitoring/pacing functions. For instance, it is estimated that when the battery has a size of 5 cc, the defibrillator can provide at least 21 months of monitoring and pacing functionality. Further, it is estimated that when the battery has a size of 3 cc, the defibrillator can provide at least 11 months of monitoring and pacing functionality. Additionally, it is estimated that when the battery has a size of 5 cc, the defibrillator can provide at least 88 sequential defibrillation shocks. Further, it is estimated that when the battery has a size of 3 cc, the defibrillator can provide at least 34 sequential defibrillation shocks.

Figure 1:
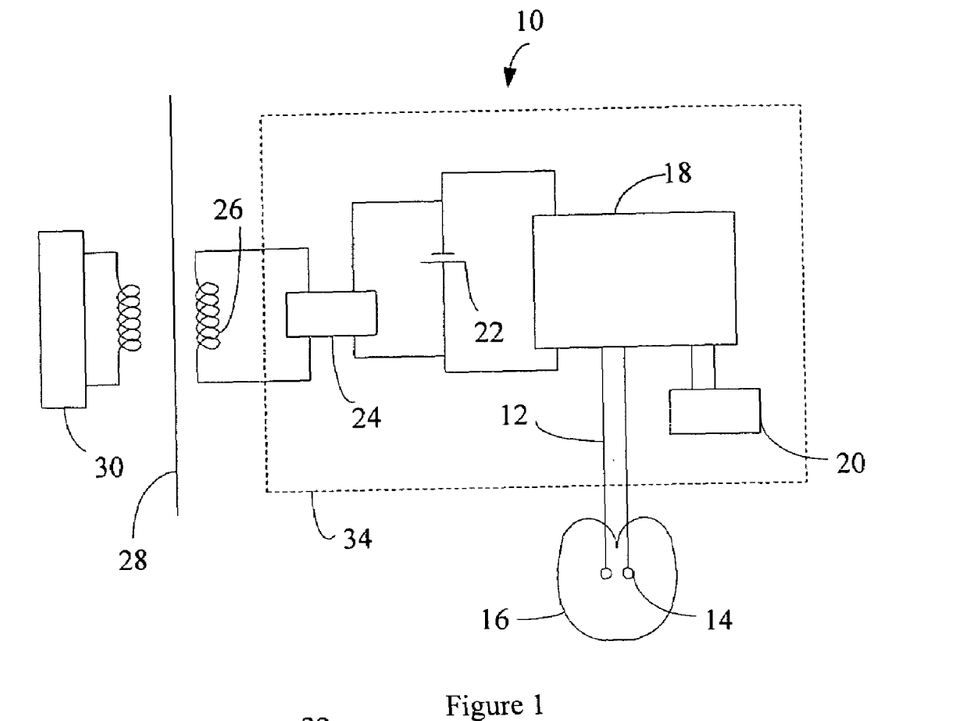
FIG. 1 is a schematic diagram of a defibrillator system.

FIG. 1 is a schematic diagram of a defibrillation system 10. The defibrillation system 10 includes lead lines 12 connected to electrodes 14 in contact with the heart. Although the defibrillation system 10 is shown with two electrodes 14, the defibrillation system 10 may include three or more electrodes 14 and/or three or more lead lines. The specific positions of the electrodes 14 relative to the heart 16 is dependent upon the requirements of the patient. For instance, the electrodes 14 can be positioned in the superior vena cava and the right ventricle of the heart. Leads may be implanted in other regions of the heart such as the left atrium and left ventricle for therapies such as pacing for congestive heart failure.

The defibrillation system 10 also includes a processing unit 18. The lead lines 12 provide electrical communication between the processing unit 18 and the electrodes 14. The processing unit 18 is also in electrical communication with capacitor circuits 20. The capacitor circuits 20 are in electrical communication with the lead lines 12. The capacitor circuits 20 include one or more capacitors (not shown) for storing energy. The processing unit 18 can cause the one or more capacitors to be discharged such that energy stored in the one or more capacitors is delivered to the heart through all or a portion of the electrodes 14.

A secondary battery 22 provides power to the processing unit 18 and the capacitor circuits 20. The secondary battery 22 is in electrical communication with recharge circuits 24. The recharge circuits 24 are in electrical communication with a coil 26 positioned under the skin 28. The battery 22 can be charged by use of an external charger circuit 30 to transfer energy to the implanted recharge circuit 24. During charging of the battery 22, the external charger circuit 30 transmits energy from a coil through the skin 28 where it is received by the implanted coil 26. The implanted coil 26 supplies the energy to the implanted recharge circuit 24. The implanted recharge circuit 24 employs the energy to charge the battery 22.

Suitable processing units 18 can include, but are not limited to, analog electrical circuits, digital electrical circuits, processors, microprocessors, digital signal processors (DSPs), computers, microcomputers, or combinations suitable for performing the monitoring and control functions. In some instances, the processing unit 18 has access to a memory that includes instructions to be executed by the processing unit 18 during performance of the control and monitoring functions.

The processing unit 18, the battery 22, the capacitor circuits 20 and the recharge circuits 24 can be located within a case 34. Although the coil 26 is show as being positioned outside of the case 34, in some instances, the coil 26 can be positioned within the case 34.

During operation of the defibrillation system 10, the defibrillation system 10 employs output from the lead lines 12 to monitor the heart and diagnose when defibrillation shocks should be provided. These monitoring functions generally drain on the order of 10 µA from the battery 22. The defibrillation system 10 can also provide pacing capabilities. The current draw on a battery 22 due to constant pacing can be estimated by assuming that pacing will use 6-V, 500-µs pulses at an impedance of 500 Ω at a rate of 70 beats/minute. Under these conditions, the energy drawn from the battery 22 will be about 2.5 mJ/min, or an average current draw of about 7 µA.

When the processing unit 18 identifies that defibrillation shocks are needed, the processing unit 18 provides the heart with one or more defibrillation shocks. To provide a defibrillation shock, the processing unit 18 employs energy from the battery 22 to charge the one or more capacitors in the capacitor circuits 20. The processing unit 18 causes these capacitors to be discharged such that energy stored in the capacitors is delivered to the heart through all or a portion of the electrodes 14 in the form of defibrillation shocks.

During the defibrillation shocks, the defibrillator requires that one or more pulses are delivered from the battery 22 to the one or more capacitors. Each pulse is generally associated with a defibrillation shock. The duration of each pulse is generally about 8 to 12 seconds with the pulses separated by about 8 to 12 seconds. In a preferred embodiment, each pulse has a duration of about 10 seconds and a separation of about 10 seconds. The defibrillator generally requires that each pulse provide at least 35 J to the one or more capacitors or at least 70 J to the one or more capacitors. In one embodiment, the defibrillator requires that each pulse provide at least 40 J to the one or more capacitors or at least 80 J to the one or more capacitors.

Although FIG. 1 illustrates the defibrillator having a single battery, the defibrillator can include more than one battery. For instance, the defibrillator can include a primary battery in addition to the secondary battery. The primary battery can be employed to provide the energy needed for monitoring and pacing while the secondary battery can provide energy for the defibrillation shocks.

Figure 2:
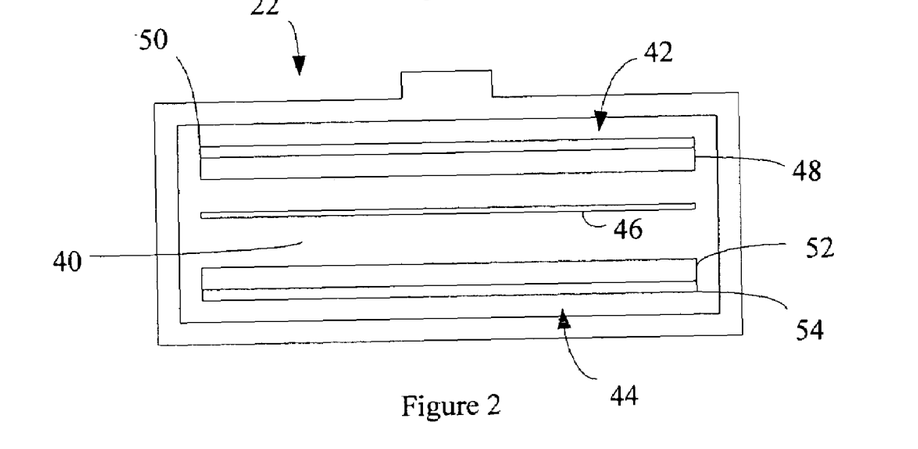
FIG. 2 illustrates a battery suitable for use in the defibrillator system of FIG. 1.

FIG. 2 is a schematic view of a suitable battery 22. The battery 22 includes an electrolyte 40 activating a cathode 42 and an anode 44. The cathode 42 and anode 44 are separated by a separator 46. The cathode 42 includes a cathode medium 48 on a cathode substrate 50. The anode 44 includes an anode medium 52 on an anode substrate 54.

The electrolyte 40 includes one or more salts dissolved in a solvent. Suitable salts for use with the electrolyte include, but are not limited to, alkali metal salts including lithium salts. Examples of lithium salts include $LiClO_4$, $LiBF_4$, $LiAsF_6$, $LiPF_6$, $LiCF_3SO_3$, $Li(CF_3SO_2)_2N$, $Li(CF_3SO_2)_3C$, $LiN(SO_2C_2F_5)_2$, lithium alkyl fluorophosphates organoborate salts and mixtures thereof. A preferred salt for use with the electrolyte include organoborate salts such as lithium bis(chelato)borates including lithium bis(oxalato)borate (LiBOB) and lithium difluoro oxalato borate (LiDfOB). Examples of suitable organoborate salts are disclosed in U.S. patent application Ser. No. 60/565,211, filed on Apr. 22, 2004, entitled "Organoborate Salt in Electrochemical Device Electrolytes" and incorporated herein in its entirety.

The solvent can be an organic liquid or an inorganic liquid. The solvent can include or consist of one or more first solvents and/or one or more second solvents. In some instance, the first solvent is a low viscosity solvent and the second solvent is a high permittivity solvent. Examples of first solvents include, but are not limited to, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy,2-methoxyethane (EME), ethyl methyl carbonate (EMC), methyl propyl carbonate, ethyl propyl carbonate, diethyl carbonate (DEC), dipropyl carbonate, and mixtures thereof. Examples of second solvents include, but are not limited to, cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methyl-2-pyrrolidone (NMP), and mixtures thereof.

In addition to the first solvents and second solvents described above or as an alternate to the first solvents and second solvents described above, the solvent can include or consists of one or more silanes and/or one or more siloxanes. Examples of suitable siloxanes include, but are not limited to, polysiloxanes and oligosiloxanes with side chains that include polyethylene oxide moieties. Other suitable siloxanes include, but are not limited to, disiloxanes, trisiloxanes, tetrasiloxanes, pentasiloxanes with side chains that include polyethylene oxide moieties. Examples of suitable disiloxanes, trisiloxanes and tetrasiloxanes are disclosed in U.S. Provisional Patent application Ser. No. 60/543,951; filed on Feb. 11, 2004; entitled "Siloxanes"; and incorporated herein in its entirety and in U.S. Provisional Patent application Ser. No. 60/543,898; filed on Feb. 11, 2004; entitled "Siloxane Based Electrolytes for Use in Electrochemical Devices"; and incorporated herein in its entirety. Examples of suitable solvents that include blends of silanes and siloxanes are disclosed in U.S. patent application Ser. No. 10/810,080; filed on Mar. 25, 2004; entitled "Electrolyte for Use in Electrochemical Devices" and incorporated herein in its entirety. Example of suitable solvents that include silanes are disclosed in U.S. Provisional Patent application serial number (Not Yet Assigned); filed on Aug. 13, 2004; entitled "Electrolyte Including Silane for use in Electrochemical Devices" and incorporated herein in its entirety.

In some instances, the electrolyte is generated so as to include one or more additives. Additives can serve a variety of different functions. For instance, additives can enhance the ionic conductivity and/or enhance the voltage stability of the electrolyte. A preferred additive forms a passivation layer on one or more electrodes in an electrochemical device such as a battery or a capacitor. The passivation layer can enhance the cycling capabilities of the electrochemical device. In one example, the passivation layer is formed by reduction of the additive at the surface of an electrode that includes carbon. In another example, the additive forms a polymer on the surface of an electrode that includes carbon. The polymer layer can serve as the passivation layer.

Suitable additives include, but are not limited to, carbonates, sulfur compounds, unsaturated hydrocarbons and nitrogen compounds. In some instances, the electrolyte includes at least one additive selected from the group consisting of: vinyl carbonate (VC), vinyl ethylene carbonate (VEC), ethylene sulfite, 1,3 dimethyl butadiene, styrene carbonate, aromatic carbonates, vinyl pyrrole, vinyl piperazine, vinyl piperidine, vinyl pyridine, and mixtures thereof. In one example, the electrolyte includes vinyl ethylene carbonate as an additive. VC is an example of an additive that can be reduced to form a passivation layer that includes a carbonate at the surface of an electrode that includes carbon. Pyridine is an example of an additive that can form a polymeric passivation layer at the surface of an electrode that includes carbon. VEC is an example of an additive that can form a passivation layer by both being reduced and forming a polymer at the surface of an electrode that includes carbon. In some conditions, certain organoborate salts, such as LiBOB and LiDfOB, can form a passivation layer. As a result, the desirability of additives may be reduced when organoborate salts are employed. A suitable concentration for an additive in the electrolyte includes, but is not limited to, concentrations greater than 0.1 wt %, greater than 0.5 wt % and/or less than 5 wt % or less than 20 wt %. In a preferred embodiment, the concentration of the additive is less than 3 wt %.

A preferred embodiment of the electrolyte is 1 M to 1.2 M $LiPF_6$ in 20 wt % to 30 wt % ethylene carbonate (EC) and 70 wt % to 80 wt % diethyl carbonate (DEC). In a preferred embodiment, the electrolyte is 1 M to 1.2 M $LiPF_6$ in 25 wt % ethylene carbonate (EC) to 75 wt % diethyl carbonate (DEC).

Suitable separators 46 include, but are not limited to, polyolefins such as polyethylene.

Suitable cathode substrates 50 include, but are not limited to, aluminum. The cathode medium 48 includes or consists of one or more cathode active materials and a binder. Suitable binders include, but are not limited to, PVdF. A suitable cathode active material includes or consists of, a lithium metal oxide. Before charging the battery 22 for the first time, the lithium metal oxide can be represented by $LiMO_2$ where M is one or more metals. In a preferred embodiment, M includes or consists of one or more components selected from a group consisting of Co, Ni, Mn, Al, Li, Sn, In, Ga, or Ti. In a preferred example of the lithium metal oxide before charging the battery for the first time, the lithium metal oxide is represented by $LiCo_xNi_yM'_zO_2$, where M'=Mn, Al, Li, Sn, In, Ga, or Ti, and $0.15 \leq x \leq 0.5$, $0.5 \leq y \leq 0.8$, and $0 \leq z \leq 0.15$, and more preferably represented by $LiCo_xNi_yAl_zO_2$ where $0.15 \leq x \leq 0.5$, $0.5 \leq y \leq 0.8$, and $0 \leq z \leq 0.05$. The cathode medium 48 can also contains a material for enhancing conductivity, such as acetylene black or graphite.

The anode medium 52 includes or consists of one or more anode active materials and a binder. The anode active material can include a carbonaceous mixture. For instance, the carbonaceous mixture can include a mixture of carbon beads, carbon fibers, and graphite flakes. The carbon beads can have shapes that approximate blocks, spheres, sphereoids, cylinders, cubes or combinations of these shapes. Carbon beads preferably have a real density of greater than 2.2 g/cc; a surface area of less than 3 $m^2/g$, more preferably less than 2 $m^2/g$, and more preferably less than 1 $m^2/g$ as measured by BET where BET is the analytical method employed to measure the specific surface area of powder based on the BET adsorption isotherm reported by Brunauer, Emmert, and Teller; and/or an average particle size of less than 40 µm and preferably 10–35 µm. The carbon beads may have a structure that is inherently rigid. Alternatively or additionally, the carbon beads may have a rigid surface layer that makes them difficult to deform. For instance, the carbon beads can have a rigid surface layer that includes hard carbon. The carbon beads provide structural support to the anode medium 52 of the present invention. The structural support helps maintain the porosity of the anode medium 52. The porosity of the anode medium 52 can enhance the contact between the electrolyte and the carbon. Additionally, the bead shape can help minimize the surface area of the graphite within the carbonaceous mixture. As a result, the carbon beads can limit the amount of lithium required to form a layer, or solid electrolyte interface (SEI) on the anode. The carbon beads generally have fewer side reactions such as electrolyte decomposition relative to other shapes of carbon materials. The carbon beads may be mesocarbon microbeads produced by subjecting mesophase spherules, produced during the carbonization of pitch, to heat treatment for graphitization. An example of the carbon beads is mesocarbon microbeads (MCMB) which are available from Osaka Gas Chemicals Co., LTD.

The carbon fibers preferably have a specific surface area of less than 5 $m^2/g$; an average particle size of less than 40 µm and preferably 10–35 µm; a d002 (layer distance) of less than 3.36 Å; and an Lc of greater than 100 nm. Carbon fibers that are too long may cause microshorts by penetrating the separator 46. The carbon fibers improves packing density and conductivity. Carbon fibers can also intensify the stiffness of the anode and reduce swelling and decomposition of the anode. The carbon fibers may be a vapor grown carbon fiber. The carbon fiber may be prepared by subjecting hydrocarbons such as benzene, methane, propane, and so on to vapor phase heat-decomposition under the presence of catalyst base plate made of Fe, Ni, Co, and so on in order to make carbon fibers deposit and grow on the base plate. Other examples are pitch carbon fibers, made from petroleum or coal pitch as a raw material through a spinning and carbonating treatment, and carbon fibers made from polyacrylonitrile (PAN), which may be used in the invention.

The graphite flakes can be natural or artificial graphite flakes. The graphite flakes can be softer than carbon beads. The flakes tend to reduce friction in the carbon mixture because the planes of carbon can slip with respect to one another, allowing the graphite flakes to fit within the spaces in the mixture. The graphite flakes can be less than 40 µm and are more preferably 10–35 µm.

Table 1 sets forth suitable ratios for the carbon beads, the carbon fibers, and the graphite flakes. The carbon bead content of the composite carbon material is preferably from 0 wt. % to 80 wt. %; the carbon fiber content of the composite carbon material is preferably from 0 wt. % to 80 wt. %; and the graphite flake content of the composite carbon material is preferably from 0 wt. % to 30 wt. %. If the carbon bead content is above 80 wt. %, the surface contact between the particles, and thus conductivity and capacity, is too low. If the fiber content is above 80 wt. %, the packing density, and thus the capacity, is decreased. Increasing the flake content above 30 wt. % can reduce battery capacity by increasing the surface area enough to provide undesirably high consumption of lithium during formation of the SEI layer. Also, a flake content above 30 wt. % may lack the structural support to keep the pores open to keep the porosity within an optimal range to allow the electrolyte to react freely with the surface of the carbonaceous material. The anode medium 52 preferably has a porosity of 30–45%, and the cathode medium 48 preferably has a porosity of 20–40%.

TABLE 1

|  | preferably | more preferably | most preferably |
| --- | --- | --- | --- |
| carbon beads | 0–80 wt % | 10–80 wt % | about 70 wt % |
| carbon fibers | 0–80 wt % | 21–80 wt % | about 22.5 wt % |
| graphite flakes | 0–30 wt % | 2–30 wt % | about 7.5 wt % |
| total |  | 100% |  |

In a preferred embodiment, the anode active material contains carbon beads, carbon fibers, and graphite flakes. Preferably, the carbon beads, carbon fibers, and graphite flakes have an average particle size of less than 40 µm, and occur in a ratio of approximately 70% carbon beads: 22.5% carbon fibers: 7.5% graphite flakes.

The binder of the anode medium 52 preferably contains no fluorine, and more preferably includes carboxymethyl batteryulose (CMC). Even more preferably, styrene butadiene rubber (SBR) is added, which imparts elasticity to the mixture. In contrast, prior art electrodes contained a PVdF binder, which was unstable and tended to break down, especially at higher temperatures, consuming Li+ in the reaction $F^-+Li^+ \rightarrow LiF$. To avoid this, the anode medium 52 of the present invention preferably uses a CMC+SBR binder that excludes fluorine. Table 2 sets forth suitable ratios for the CMC and SBR in the binder. As an alternative to a binder that consists of CMC and SBR, a different fluorine excluding binder or a fluorine-containing binder that is more stable than PVdF in the battery's operating range may be used. Another advantage of using a binder containing SBR as compared with PVdF is that SBR binds to more area of the graphite mixture than does PVdF; therefore, the exposed surface area of graphite is minimized, minimizing electrolyte decomposition at the graphite surface. A dispersion in water of the carbonaceous mixture, CMC, and SBR can be made to form a slurry that can be conveniently coated onto a metal foil substrate.

TABLE 2

|  | preferably | more preferably | most preferably |
| --- | --- | --- | --- |
| CMC | 0 to 30% | 0 to 10% | about 1.5% |
| SBR | 0 to 30% | 0 to 5% | about 2.5% |

A suitable material for the anode substrate 54 includes, but is not limited to, titanium, a titanium alloy or stainless steel. In a preferred embodiment, the anode substrate 54 is about 12 µm thick.

During charge of the battery, lithium intercalates at the anode to form $C_6Li_n$. Before the initial charge of the battery, the anode active material can exclude lithium. Accordingly, n can be 0 before the initial charge of the battery. The amount of active material in the anode is preferably selected such that charging the battery increases n to 0.5 to 0.84. For instance, for a given amount of cathode medium 48, the amount of the anode medium 52 (i.e. the thickness of the anode medium) can be increased to reduce the level to which n rises on charging or decreased to increase the level to which n rises on charging. Preferably the amount of anode medium 52 is selected such that n increases to about 0.6. When n is increases to too high, the opportunity for lithium plating on the anode increases. This mechanism tends to reduce battery calendar life and cycle. On the other hand, when the increase in n is not sufficient, the battery voltage and capacity are low. Values of n=0.5 to 0.8, and most preferably about 0.6, have been found to be a good compromise between calendar life, battery voltage and capacity.

The lithium in the cathode active material deintercalates during charge of the battery. Accordingly, the cathode active material is initially represented by $Li_{1-p}MO_2$ with p=0. Deintercalation of the lithium during charge of the battery causes the value of p to increase during charge of the battery. The amount of the cathode active material is selected such that p is 0.6 to 0.8 at the maximum charge state. Preferably p is about 0.7 at the maximum state of charge. In a preferred embodiment, the cathode active material includes $Li_{0.3}Co_xNi_yAl_zO_2$ at maximum charge where $0.15 \leq x \leq 0.5$, $0.5 \leq y \leq 0.8$, and $0 \leq z \leq 0.05$. When p is too high, electrolyte oxidation occurs.

To make an anode, a mixture of carbon beads, carbon fibers, and graphite flakes, a binder, and water are mixed together to form a slurry. The slurry is applied to both sides of metal foil and dried. In a preferred method, carbon beads, carbon fibers, and graphite flakes in the amounts described above are first combined. Then the binder, preferably CMC, 2% in water, is added and mixed. Following that, SBR, 40% in water, is preferably added with additional water, then mixed to form a slurry having the mass percents of CMC and SBR as indicated above. A 12-μm titanium foil substrate is coated with the slurry, then dried by evaporating the water off using heat, then rolled.

Although FIG. 2 illustrates the battery as including one anode and one cathode, the battery can include more than one anode and/or more than one cathode with the anodes and cathodes each separated by a separator. Additionally, the electrodes in the battery can be a stacked configuration or a wound configuration. Because the battery can have a variety of different geometries, the battery volume numbers used in the application can be determined by liquid displacement.

Additionally, the battery is preferably hermetically sealed. Hermetic sealing can reduce entry of impurities into the battery. As a result, lithium consumption and active material degradation reactions due to impurities is reduced. The reduction in impurity induced lithium consumption can stabilize battery capacity.

EXAMPLE 1

Anodes were generated by mixing Mesocarbon Microbeads (MCMB, Osaka gas Co., Ltd., 25–28), vapor grown carbon fiber and graphite flakes (MCF, Petoca Materials Ltd.) so as to provide a carbon mixture having 70 wt % carbon beads, 22.5 wt % carbon fibers and 7.5 wt % graphite flakes. Carboxymethylcellulose (CMC, 2 wt % CMC in water) is added to the carbon mixture and mixed. Styrene butadiene rubber (SBR, 40 wt % SBR in water) is further added and mixed to form a slurry having a CMC:SBR:carbon mass ratio of about 1.5:2.5:96. The slurry was coated on a 12-μm titanium foil substrate. The result was dried and pressed to about a 196 μm thickness using a roll press.

Cathodes were generated by mixing $LiNi_{0.8}Co_{0.15}Al_{0.05}O_2$ (Toda Industry Co., Ltd., CA1505N), a 12 wt % solution of PVdF in n-methyl pyrolidone (NMP, Kureha Co., Ltd., PVdF1120), acetylene black and graphite (Timcal Co., Ltd., SFG6) to provide a mixture that was 84 wt % $LiNi_{0.8}Co_{0.15}Al_{0.05}O_2$, 4 wt % acetylene black, 4 wt % graphite and 8 wt % PVdF. The mixture was coated on 20 um thick of aluminum foil substrate with a doctor blade. The result was dried and pressed down to a 156 μm thickness using a roll press.

An electrolyte was prepared by dissolving $LiPF_6$ to 1.2 M in a 25 wt %/75 wt % mixture of ethylene carbonate (EC)/diethyl carbonate (DEC). Batteries (prismatic. cells/rectangular) were prepared by employing the electrolyte to active the anode and cathode with a polyethylene (Tonen) separator positioned between the anode and the cathode.

EXAMPLE 2

Figure 3:
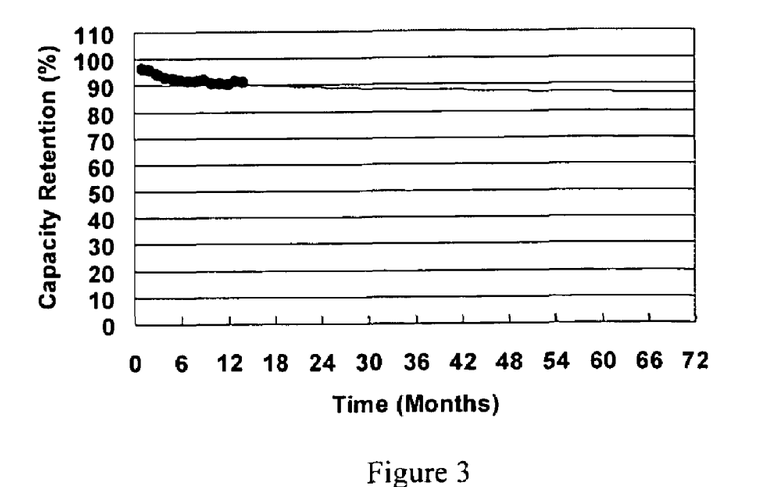
FIG. 3 illustrates the discharge capacity retention versus storage time for batteries according to FIG. 2 that were charged to a 100% state of charge (SOC) of 4.1 V and stored at 37° C.

The batteries of Example 1 were tested for calendar life. The batteries were charged to a 100% state of charge (SOC) of 4.1 V and stored at 37° C. The negative potential was approximately 0.1 V. The capacity of the batteries was checked every month. The capacity check included discharging the batteries to 2.5 V at 0.5 C, recharging the batteries to 4.1V at 0.5 C, followed by constant voltage charging at 4.1V to a 0.05C cutoff current, and then performing the capacity testing by discharging the batteries to 2.5 V at 0.5 C. The capacity check was performed at room temperature after allowing the batteries to equilibrate at room temperature for at least 2 hours. These steps extracted the effects of self-discharge from the results. FIG. 3 illustrates the capacity retention results plotted versus storage time for 14 months. At twelve months, the permanent capacity loss due to storage was less than 11%. For instance, the permanent capacity loss due to storage was about 10% at twelve months. This data follows a logarithmic trend, fitting with an $R^2$ value of about 0.91. By extrapolation of the logarithmic fit, it is expected that the batteries will have over 85% retention after 6 years of storage at 37° C.

EXAMPLE 3

Figure 4A:
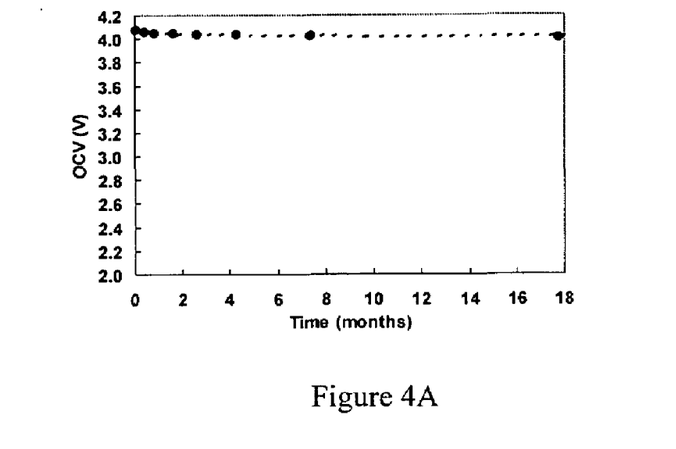
FIG. 4A illustrates the voltage versus time data for a battery that was charged to a 100% state of charge (SOC) of 4.1 V and then stored without load at 37° C.
Figure 4B:
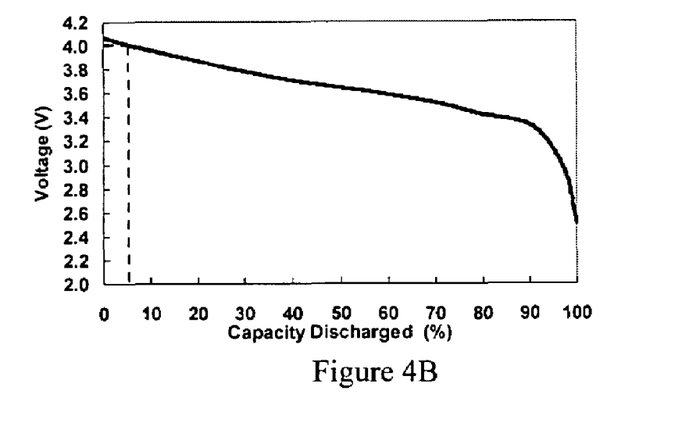
FIG. 4B is an approximate open circuit voltage versus discharge capacity data for the battery of FIG. 4A.

The batteries of Example 1 were tested for self-discharge. A first battery was charged to a 100% state of charge (SOC) of 4.1 V and then stored without load at 37° C. Instead of discharging the first battery to test for remaining discharge capacity, the voltage was checked at various intervals. After about 18 months, the voltage had dropped to 4.002 V. FIG. 4A presents the resulting voltage versus time data. The illustrated voltage is also known as the open circuit voltage (OCV). To determine the capacity associated with each voltage in FIG. 4A, a second battery was discharged at a very slow rate of C/200. FIG. 4B presents the voltage versus discharge capacity data for this battery. At C/200, the voltage levels shown in FIG. 4B very closely approximate the open circuit voltage (OCV) of the first battery. As a result, the voltage of FIG. 4B can be associated with the voltage of FIG. 4A in order to generate a correlation between the storage time of the first battery and the remaining discharge capacity. As is evident in FIG. 4B, the 18 month drop to 4 volts correlates to a self-discharge of about 5%. Accordingly, the battery has less-than 6% self discharge when stored for six months at 37° C.

Correcting for the 10% of permanent capacity loss at one year due to calendar fade (See Example 2), the battery would have approximately 15% of combined loss from self-discharge and calendar fade when stored fully charged at 37° C. for one year. This corresponds to an 85% storage capacity retention, with 5% capacity which is recoverable by recharging. Since it is known that capacity loss due to storage at high temperature can generally be approximated by a logarithmic fit, a large drop in the rate of capacity loss is expected after the first year.

EXAMPLE 4

The batteries of Example 1 were tested for cycle life at different depths of discharge (DOD). For instance, the batteries were cycled to a 20%, 40%, 80%, and 100% DOD where a 100% DOD was a discharge to 2.5 V. For all DODs, the batteries were charged to 4.1 V with constant current at a 0.5 C rate, and then a constant voltage charge at 4.1 V to a 0.05 C cutoff current. The batteries were then discharged to the desired DOD at a 0.5 C rate. This cycle of charge and discharge was repeated at 37° C. At every 100 cycles, a full capacity check (100% DOD) was performed for all batteries at room temperature.

Figure 5A:
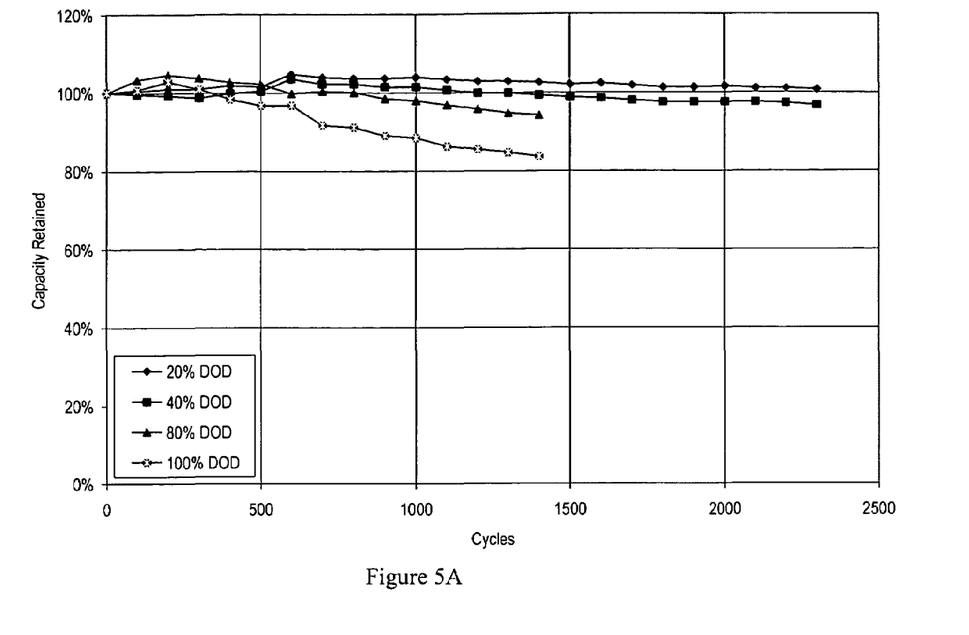
FIG. 5A illustrates the discharge capacity retention versus cycle number for batteries repeatedly cycled between fully charged and a particular depth of discharge.

FIG. 5A shows the discharge capacity retention versus cycle number for each depth of discharge. Table 3 sets forth some of the data for discrete points in FIG. 5A. As is evident in Table 3, when a 100% DOD is used, the batteries show a discharge capacity retention of at least 88% after 1000 cycles. When an 80% DOD is used, the batteries show a discharge capacity retention of at least 97% after 1000 cycles. Further, when a 40% DOD is used, the batteries show a discharge capacity retention of at least 98% after 1500 cycles. Accordingly, the use of lower DODs greatly improves cycle life performance and capacity retention for the batteries. For instance, using a DOD of 80% instead of 100%, raises the capacity retention of the battery from 89% to 98% after about 1000 cycles. Accordingly, the batteries can provide a discharge capacity retention of at least 90% after 1000 cycles; at least 95% after 1000 cycles or even at least 97% after 1000 cycles when cycled between 100% SOC and a DOD of less than 80%.

TABLE 3

| DOD (%) | Cycle Number | Capacity Retention (%) |
|---|---|---|
| 20 | 1500 | 102.1 |
| 40 | 1500 | 98.8 |
| 80 | 1000 | 98.0 |
| 100 | 1000 | 88.5 |

Figure 5B:
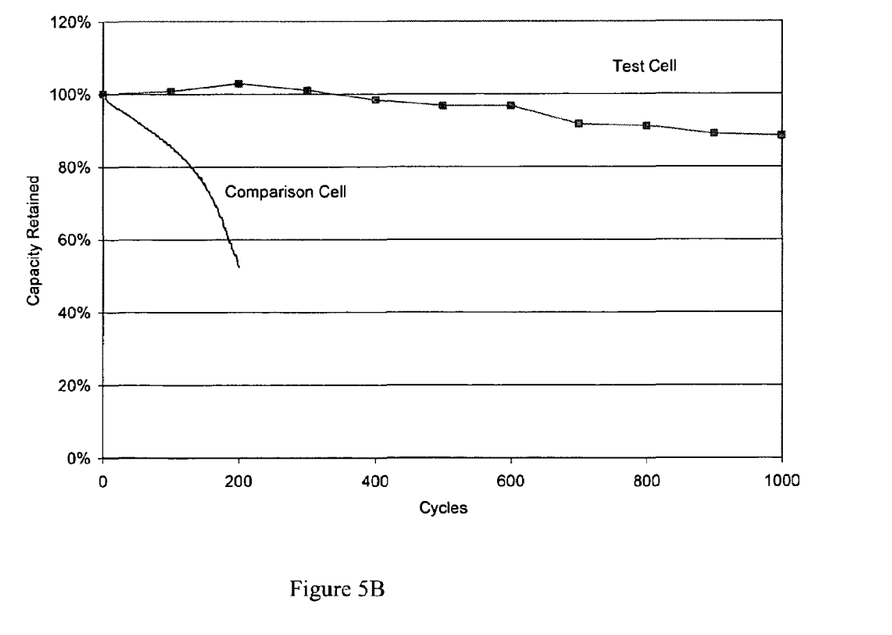
FIG. 5B compares the discharge capacity retention versus cycle number data from FIG. 5A with discharge capacity retention versus cycle number data from a commercially available battery.

For the purposes of comparison, the cycle performance of the batteries of Example 1 was compared to a commercially available Sony battery model number US17670GR. This comparison battery includes a graphite anode and a cathode that includes $LiCoO_2$. The comparison battery was cycled between 4.2 V and 2.7 V. FIG. 5B compares the discharge capacity retention versus cycle number data for the batteries of Example 1 and the comparison battery. The comparison battery had a discharge capacity retention less than 60% after only 200 cycles. In contrast, the batteries of Example 1 had a discharge capacity retention of at least 87% after 1000 cycles and more specifically at least 88% after 1000 cycles. The above cycle performance is suitable for use in the defibrillator.

EXAMPLE 5

Figure 6A:
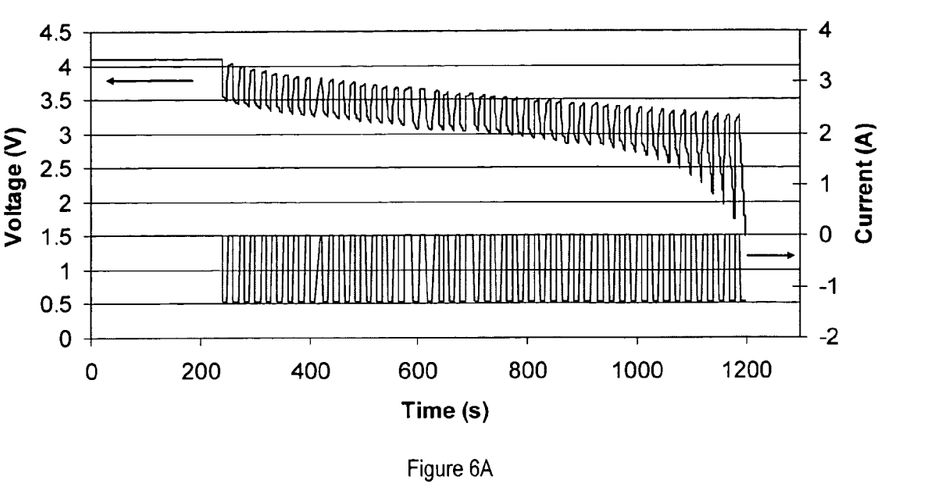
FIG. 6A shows a voltage profile of a battery during a pulse sequence where each pulse approximates the pulse needed to provide a defibrillation shock.

The ability of the example 1 batteries to provide the pulses needed for the defibrillation shocks was tested. Pulse cycling was employed to test a battery for its ability to repeatedly discharge a series of pulses. The battery was held at about 37° C. for all of the testing in this example. To check the number of sequential 40 J pulses the cell was capable of discharging, the battery was charged at 100 mA to 4.1 V, followed by constant voltage charge with a 10 mA cutoff. After 5 minutes rest, the battery was discharged in sequential pulses of 1.3 A (to get approximately 40 J energy per pulse) until the closed-circuit voltage (CCV) reached a cutoff of 1.5 V. For this pulse train, the pulses had durations of 10 seconds and were separated by 10 second rests. FIG. 6A shows a voltage profile of the battery during this pulse sequence, which consists of 46 pulses. The lowest operational voltage of defibrillators is generally about 1.5 V. FIG. 6 shows that the battery was able to provide more than 40 pulses before falling below the lowest operational voltage.

Figure 6B:
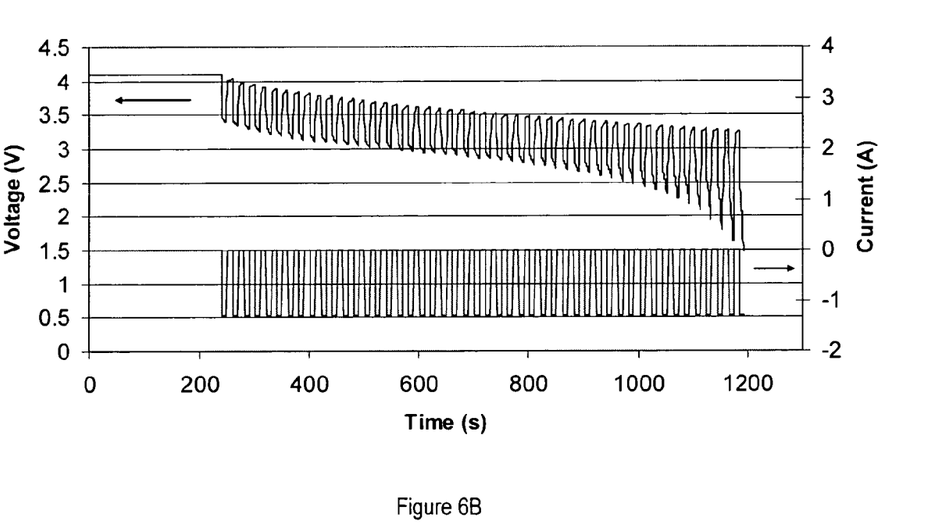
FIG. 6B shows a voltage profile of a battery during a pulse sequence where each pulse approximates the pulse needed to provide a defibrillation shock.

After the above pulse-check, the battery was tested by repeating pulse trains. The batteries were charged at 100 mA to 4.1 V, followed by discharging sequential 50 J pulses down to a cutoff of 2.7 V CCV. The pulses were for durations of 10 seconds and were separated by 10 seconds rests. This cycle of charging and discharging was repeatedly performed at 37° C. for three months, which included 2000 of these cycles. After the three month time period, the pulse-cycling used to generate FIG. 6A was repeated to check the number of 1.3 A 10 seconds pulses that could be discharged sequentially. FIG. 6B shows the voltage profile of the battery during this pulse sequence, which consists of 47 pulses. A comparison of FIG. 6B and FIG. 6A illustrates that the battery retained the pulse discharge ability after pulse cycling for a period of three months and for 2000 cycles.

In addition to maintaining its pulse capability, the battery maintained most of its initial capacity during a full discharge. For a discharge from 4.1 V to 2.7 V the battery achieved a discharge capacity retention of about 93% capacity retention. As a result, this battery can repeatedly provide the defibrillation shocks without significant loss of pulse capabilities.

EXAMPLE 6

The batteries prepared in Example 1 had a volume of about 3.04 CC and a capacity of about 190 mAh based on cycling at a 0.5 C rate, between 2.5 V and 4.1 V, at room temperature, 23° C. The results were scaled to approximate the capacity and performance of the same batteries at battery volumes of 3 cc, 4 cc, 5 cc and 6 cc. For each size of battery, the number of pulses that can be provided sequentially without the battery falling below the minimum operating voltage of the defibrillator (generally about 1.5 V) was estimated with each pulse having at least 40 J energy; a ten second duration; and being separated from the next pulse by ten seconds. The results are set forth in Table 4. In accordance with these results, it is estimated that a battery with a volume less than or equal to 3 cc at full charge before implantation of the defibrillator is able to provide to the one or more capacitors a series of 34 or more pulses that each have at least 40 J provided over ten seconds with each of the pulses separated by ten seconds. Further, it is estimated a battery with a volume less than or equal to 4 cc at full charge before implantation of the defibrillator is able to provide to the one or more capacitors a series of 66 or more pulses that each have at least 40 J provided over ten seconds with each of the pulses separated by ten seconds. Additionally, it is estimated that a battery with a volume less than or equal to 5 cc at full charge before implantation of the defibrillator is able to provide to the one or more capacitors a series of 91 or more pulses that each have at least 40 J provided over ten seconds with each of the pulses separated by ten seconds. In some instances, a battery is able to provide more pulses than is listed in Table 4.

The number of pulses that can be provided sequentially without the battery falling below the minimum operating voltage of the defibrillator (generally about 1.5 V) and with each pulse having at least 80 J energy is also estimated and the results set forth in Table 4. In accordance with these results, it is estimated a battery with a volume less than or equal to 4 cc at full charge before implantation of the defibrillator is able to provide to the one or more capacitors a series of 9 or more pulses that each have at least 80 J provided over ten seconds with each of the pulses separated by ten seconds. Additionally, it is estimated that a battery with a volume less than or equal to 5 cc at full charge before implantation of the defibrillator is able to provide to the one or more capacitors a series of 23 or more pulses that each have at least 80 J provided over ten seconds with each of the pulses separated by ten seconds. In some instances, a battery is able to provide more pulses than listed in Table 4.

The number of defibrillation shocks delivered during a defibrillation event can be as few as one but can increase depending on how quickly the shocks convert the arrhythmia to a normal rhythm. During unusual circumstances referred to as "arrhythmia storms," as many as 10 to 15 shocks may be needed in a short period of time, such as in a 1 to 24 hour period. As is evident from the above discussions, a battery as small as 3 cc can provide the pulsing performance when the defibrillator employs 40 J pulses. For instance, it is estimated that when the defibrillator has a battery with a volume of less than or equal to 3 cc, the defibrillator can provide at least 34 sequential defibrillation shocks. Further, it is estimated that when the defibrillator has a volume of less than or equal to 4 cc, the defibrillator can provide at least 66 sequential defibrillation shocks. Additionally, it is estimated that when the defibrillator has a volume of less than or equal to 5 cc, the defibrillator can provide at least 91 sequential defibrillation shocks. When the defibrillator employs 80 J pulses, a slightly larger battery may be required to achieve the desired pulsing performance. For instance, it is estimated that when the defibrillator has a volume of less than or equal to 4 cc, the defibrillator can provide at least 9 sequential defibrillation shocks. Additionally, it is estimated that when the defibrillator has a volume of less than or equal to 5 cc, the defibrillator can provide at least 23 sequential defibrillation shocks.

The data developed from the batteries of Example 1 was also employed to estimate the capacity and monitoring/pacing endurance of the same batteries at battery volumes of 3 cc, 4 cc, 5 cc and 6 cc. The results of these estimates are also set forth in Table 4. It is estimated that at full charge a battery having a volume of 5 cc has a capacity of at least 320 mAh; that a battery having a volume of 4 cc has a capacity of at least 250 mAh and that a battery having a volume of 3 cc has a capacity of at least 177 mAh. These capacity values are determined by discharging at C/2 rate from 4.1V to 2.5V.

The duration of each size of battery when continuously discharged from a fully charged state for the first time at 20 $\mu$A to 2.7 V is also estimated and set forth in Table 4. The 20 $\mu$A draw used to develop the data approximates the current demand needed for the defibrillator to provide monitoring and pacing functions. For instance, 20 $\mu$A represents 10 $\mu$A for monitoring functions, 7 $\mu$A for pacing functions and 3 $\mu$A for self discharge. As evident in Table 4, a battery having a volume of 5 cc is estimated to last at least 21 months without recharging; a battery having a volume of 4 cc will last at least 16 months without recharging; and a battery having a volume of 3 cc will last at least 11 months without recharging. In view of these results, it is estimated that a defibrillator having a 5 cc battery can provide monitoring and pacing functions for at least 21 months without recharging the battery. Further, it is estimated that a defibrillator having a 4 cc battery can provide monitoring and pacing functions for at least 16 months without recharging the battery. Additionally, it is estimated that a defibrillator having a 3 cc battery can provide monitoring and pacing functions for at least 11 months without recharging the battery. The above results illustrate that the secondary battery can satisfy both the low current monitoring/pacing requirements of the defibrillator and the high energy pulse requirements of the defibrillator.

TABLE 4

| Volume (cc) | Capacity (mAh) | # of sequential pulses w/ at least 40 J | # of sequential pulses w/ at least 80 J | Total # of 40 J available (based on capacity) | Total # of 80 J available (based on capacity) | Duration of battery with 20 $\mu$A discharge (months) |
|---|---|---|---|---|---|---|
| 3 | 187 | 37 | 1 | 53 | 19 | 13 |
| 4 | 261 | 69 | 11 | 78 | 33 | 18 |
| 5 | 335 | 96 | 27 | 103 | 46 | 23 |
| 6 | 410 | 118 | 44 | 128 | 59 | 28 |

The data for some of the above examples was developed using an ARBIN INSTRUMENTS, Inc. cycler.

In instances where time data is provided in months, 30 days was used as the duration of each month.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A defibrillator, comprising:
   a rechargeable battery having a volume less than 5 cc, the battery being the only battery in the defibrillator;
   one or more capacitors configured to store electrical energy from the battery in an amount sufficient to provide one or more defibrillation shocks; and
   a processing unit configured to control the storage of electrical energy in the one or more capacitors and to control the discharge of the electrical energy from the one or more capacitors.

2. The defibrillator of claim 1, wherein the battery has a total volume of less than 4 cc.

3. The defibrillator of claim 1, wherein the battery has a total volume of less than or equal to 3 cc.

4. The defibrillator of claim 1, wherein a chemistry of the battery is selected such that the battery has self-discharge characteristics for which the temporary capacity loss due to self-discharge is less than 6% of the cell discharge capacity after being stored fully charged at 37° C. for six months.

5. The defibrillator of claim 1, wherein a chemistry of the battery is selected such that the battery has calendar fade characteristics that provide a permanent discharge capacity loss of less than 11% after being stored fully charged at 37° C. for twelve months.

6. The defibrillator of claim 1, wherein a chemistry of the battery is selected such that the battery has at least 87% discharge capacity retention after being repeatedly charged and discharged for more than 1000 cycles, each cycle including charging to 4.1V with constant current at a 0.5 C rate followed by a constant voltage charge at 4.1V to a 0.05 C cutoff current followed by discharge to 2.5 V at a 0.5 C rate.

7. The defibrillator of claim 1, wherein the battery has a volume less than or equal to 3 cc and before implantation of the defibrillator and at full charge, the battery is configured to provide to the one or more capacitors a series of 34 or more pulses that each have at least 40 J provided over ten seconds with each of the pulses separated by ten seconds.

8. The defibrillator of claim 1, wherein the battery has a volume less than or equal to 4 cc and before implantation of the defibrillator and at full charge, the battery is configured to provide to the one or more capacitors a series of 66 or more pulses that each have at least 40 J provided over ten seconds with each of the pulses separated by ten seconds.

9. The defibrillator of claim 1, wherein the battery has a volume less than or equal to 5 cc and before implantation of the defibrillator and at full charge, the battery is configured to provide to the one or more capacitors a series of 91 or more pulses that each have at least 40 J provided over ten seconds with each of the pulses separated by ten seconds.

10. The defibrillator of claim 1, wherein the battery has a volume less than or equal to 5 cc and before implantation of the defibrillator and at full charge, the battery is configured to provide to the one or more capacitors a series of 96 or more pulses that each have at least 40 J provided over ten seconds with each of the pulses separated by ten seconds.

11. The defibrillator of claim 1, wherein the battery has a volume less than or equal to 4 cc and before implantation of the defibrillator and at full charge, the battery is configured to provide to the one or more capacitors a series of 9 or more pulses that each have at least 80 J provided over ten seconds with each of the pulses separated by ten seconds.

12. The defibrillator of claim 1, wherein the battery has a volume less than or equal to 5 cc and before implantation of the defibrillator and at full charge, the battery is configured to provide to the one or more capacitors a series of 23 or more pulses that each have at least 80 J provided over ten seconds with each of the pulses separated by ten seconds.

13. The defibrillator of claim 1, wherein a chemistry of the battery is selected such that before implantation of the defibrillator and at full charge the battery has a capacity of at least 300 mAh.

14. The defibrillator of claim 1, wherein a chemistry of the battery is selected such that before implantation of the defibrillator and at full charge the battery has a capacity of at least 235 mAh.

15. The defibrillator of claim 1, wherein a chemistry of the battery is selected such that before implantation of the defibrillator and at full charge the battery has a capacity of at least 165 mAh.

16. The defibrillator of claim 1, wherein the battery includes one or more anodes with an anode active material represented by $C_6Li_n$ with n=0 before the initial charge of the battery and one or more cathodes with a cathode active material represented by $Li_{1-p}MO_2$ where M is one or more metals and p=0 before the initial discharge of the battery, the anode active material and the cathode active material being present in an amount such that at full charge n increases to 0.5 to 0.8 and p increases to 0.6 to 0.8.

17. The defibrillator of claim 16, wherein M includes one or more components selected from a group consisting of Co, Ni, Mn, Al, Li, Sn, In, Ga, or Ti.

18. The defibrillator of claim 16, wherein the one or more anodes exclude lithium before initially charging the battery.

19. The defibrillator of claim 1, wherein the battery includes one or more cathodes that each include a lithium metal oxide.

20. The defibrillator of claim 1, wherein before initially charging the battery, the battery includes one or more cathodes that each include lithium metal oxide represented by $LiCo_xNi_yM'_zO_2$, where M'=Mn, Al, Li, Sn, In, Ga, or Ti, and $0.15 \leq x \leq 0.5$, $0.5 \leq y \leq 0.8$, and $0 \leq z \leq 0.15$.

21. The defibrillator of claim 1, wherein the battery includes one or more anodes that each include carbon beads.

22. The defibrillator of claim 1, wherein the battery includes one or more anodes that each include carbon fibers.

23. The defibrillator of claim 1, wherein the battery includes one or more anodes that each include graphite flakes.

24. The defibrillator of claim 1, wherein before initially charging the battery, the battery includes one or more anodes that each include at least two components selected from the group consisting of carbon beads, carbon fibers, and graphite flakes.

25. The defibrillator of claim 1, wherein before initially charging the battery, the battery includes carbon beads, carbon fibers, and graphite flakes.

26. The defibrillator of claim 1, wherein before initially charging the battery, the battery includes one or more cathodes that each include lithium metal oxide represented by $LiCo_xNi_yAl_zO_2$ where $0.15 \leq x \leq 0.5$, $0.5 \leq y \leq 0.8$, and $0 \leq z \leq 0.05$.

* * * * *